(12) United States Patent
Schmelzeisen-Redeker et al.

(10) Patent No.: US 6,679,852 B1
(45) Date of Patent: Jan. 20, 2004

(54) SYSTEM FOR WITHDRAWING BODY FLUID

(75) Inventors: Guenther Schmelzeisen-Redeker, Lorsch (DE); Frank Deck, Niederkirchen (DE); Richard Forster, Pfreimd (DE); Thomas Weiss, Mannheim (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/614,269

(22) Filed: Jul. 12, 2000

(30) Foreign Application Priority Data

May 26, 2000 (DE) .......................... 100 26 170

(51) Int. Cl.[7] .................................. A61B 5/00
(52) U.S. Cl. .................. 600/583; 600/573; 606/181
(58) Field of Search ................. 600/573, 583; 606/181, 182, 183

(56) References Cited

U.S. PATENT DOCUMENTS

| | | | |
|---|---|---|---|
| 3,626,929 A | 12/1971 | Sanz et al. ................ | 128/2 R |
| 5,014,718 A | 5/1991 | Mitchen .................... | 128/771 |
| 5,163,442 A | 11/1992 | Ono ......................... | 128/760 |
| 5,318,584 A | 6/1994 | Lange et al. .............. | 606/182 |
| 5,582,184 A | 12/1996 | Erickson et al. .......... | 600/576 |
| 5,857,983 A | 1/1999 | Douglas et al. ........... | 600/583 |
| 5,893,870 A | 4/1999 | Talen et al. ............... | 606/201 |
| 5,951,493 A | 9/1999 | Douglas et al. ........... | 600/583 |
| 6,059,794 A | 5/2000 | Webb ....................... | 606/120 |

FOREIGN PATENT DOCUMENTS

| | | |
|---|---|---|
| JP | 9266889 | 10/1997 |
| JP | 9313465 | 12/1997 |
| WO | WO 92/02175 | 2/1992 |
| WO | WO 97/08986 | 3/1997 |
| WO | WO 98/24366 | 6/1998 |

*Primary Examiner*—Thomas Denion
*Assistant Examiner*—Ching Chang
(74) *Attorney, Agent, or Firm*—Jill L. Woodburn; Richard T. Knauer

(57) ABSTRACT

System for withdrawing body fluid from a body part in particular the finger pad, comprising a compression unit that can be deformed when the body part is pressed against it and increases the internal pressure in a region of the body part, and a withdrawal device. Deformation of the compression unit partially converts the primary pressing movement into a secondary movement which leads to an increase in the internal pressure in a region of the body part. The invention also comprises a system for stimulating the outflow of body fluid using a deformable compression unit.

21 Claims, 3 Drawing Sheets

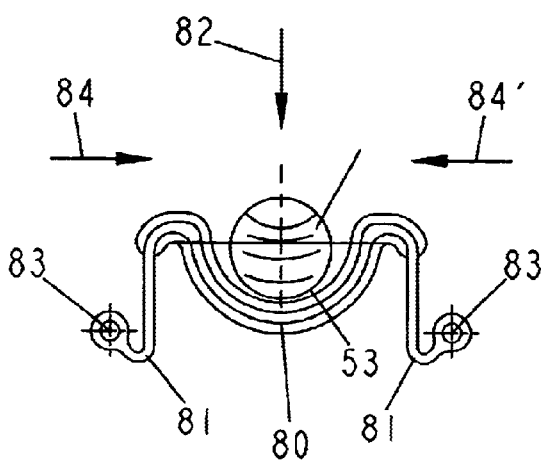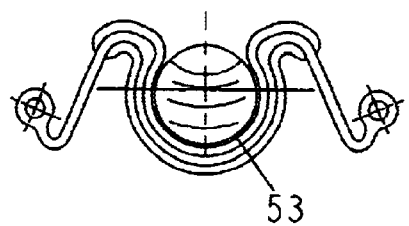
FIG. 1A  FIG. 1B
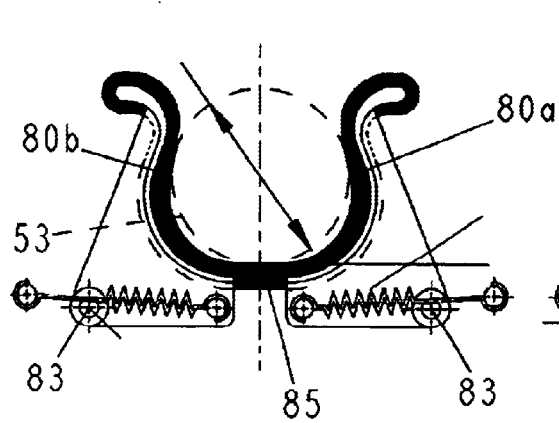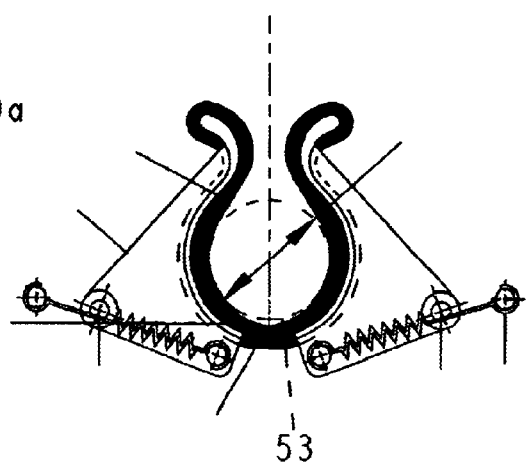
FIG. 2A  FIG. 2B
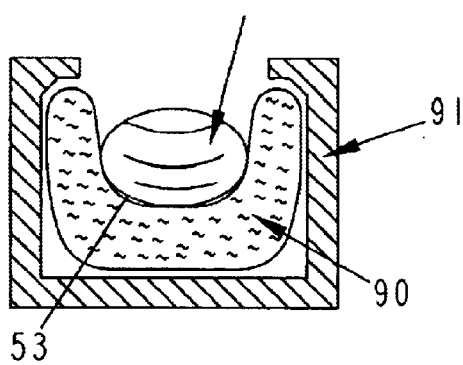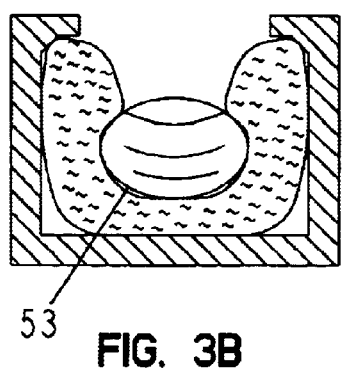
FIG. 3A  FIG. 3B

SYSTEM FOR WITHDRAWING BODY FLUID

BACKGROUND AND SUMMARY OF THE INVENTION

The present invention concerns a system for withdrawing body fluid from a part of the body, especially the finger pad. Body fluids are primarily withdrawn for a subsequent analysis in order to diagnose diseases or to monitor the metabolic state of a patient. Such a withdrawal is carried out especially by diabetics in order to determine the blood sugar concentration. The aim of such a blood-sugar check that is usually carried out several times daily is to avoid hypoglycaemic states as well as hyperglycaemic states. In the case of a hypoglycaemia the patient can fall into a coma and even die since the brain is no longer adequately supplied with glucose. In contrast hyperglycaemic states can lead to long-term side-effects such as blindness, gangrenes and such like.

Consequently a frequent monitoring of the blood sugar level is an undisputed necessity. It is therefore obvious that there is an urgent need for sampling systems which are easy to operate by the user and are above all largely free of pain.

Already blood sampling systems have been known for some time in the prior art which allow the patient or hospital staff to carry out a withdrawal in a simple manner. A device suitable for this is for example the commercially available SOFTCLIX® whose manner of operation is described in U.S. Pat. No. 5,318,584. This device provides an adjustment means for the depth to which a lancet is inserted into the tissue. Hence the patient can select the minimum puncture depth which enables a just sufficient quantity of blood to be obtained for a subsequent analysis and thus keep the incision pain very low. After the patient has produced a skin opening by piercing, he has to massage or press his finger in order to draw sufficient blood from the puncture wound especially with small puncture depths. This operation which is frequently referred to as "milking" by diabetics can hitherto only be avoided when the puncture is very deep and correspondingly unpleasant for the patient and can lead to major scarring on the sensitive finger tips. Devices known in the prior art attempt to stimulate the outflow of blood by applying a vacuum but this has proven to be not very efficient.

Devices are also known in the prior art in which a so-called stimulator with a ring depresses the skin surface surrounding an incision site. Such a device for obtaining interstitial liquid is described for example in U.S. Pat. No. 5,582,184. The document shows that pressure is only applied from one side of the body and hence the body part is not enclosed by the device. Only small amounts of fluid can be obtained with the device that are not adequate for commercial analytical systems.

Another device is known from U.S. Pat. No. 5,857,983 in which a cannula is inserted into the skin surface and the skin surface surrounding the site of incision is repeatedly depressed using a so-called stimulator in order to press body fluid into the cannula. Like the above-mentioned document a rigid ring is used in this device to depress the skin surface. The amounts of body fluid that can be obtained with this device are also small and thus inadequate for conventional analytical systems.

A device is known from the document U.S. Pat. No. 3,626,929 in which a finger is clamped before blood withdrawal between a lever and a finger support. The finger support is moved by a motor in order to result in a massaging proximal to the incision site. For the withdrawal the user's finger is pressed against a flexible cap in which needles and a fluid channel are located. A disadvantage of this device is that the needles for the withdrawal remain in the body and that in this state the finger support is moved. This results in movement of the needles in the finger which usually leads to considerable pain. In addition it is extremely unlikely that blood will emerge while there is a needle in the finger since the channel is closed by the needle. A collecting container is shown in FIGS. 11 and 12 which has a flexible pressure-application region. However, due to the shape of the pressure-application region which widens conically towards the finger there is no conversion of a primary pressure-application movement into a lateral movement which squeezes the sampling region together.

Systems are also known in the prior art in which a finger from which blood is to be withdrawn is inserted into an inflatable cuff in such a manner that the finger tip protrudes from the cuff. Inflating the cuff ties off the finger which leads to blood congestion. Such devices are described in the Japanese documents JP 9313465 and JP 9266889. However, users find these devices disagreeable since inflation of the cuff is controlled by the device and hence deprives the user of control over his finger. These devices also have technical disadvantages since pumps etc. are required to produce blood congestion which complicate the apparatus and also have quite considerable energy requirements.

A device for tying off the finger tip is described in the U.S. Pat. No. 5,893,870. It is intended that the user himself carries out the tying off and then removes blood from the finger tip with a lancing device. In this procedure the user consequently has to carry out numerous handling steps with the result that the process has hardly any advantage over the current conventional procedure in which firstly an incision is made and the finger is subsequently massaged by the user.

The object of the present invention was to provide a system for withdrawing body fluid which, using small puncture depths, yields an adequate amount of body fluid, in particular blood. An additional object of the invention was to provide a system which can be easily operated and has a simple construction. Simplicity in this sense means in particular that the number of operating steps that are required is as small as possible.

The present invention concerns a system for withdrawing body fluid from a part of the body in particular a finger pad comprising the following elements:

a deformable compression unit against which the part of the body is pressed in a primary direction and partially converts the applied pressure into a movement in a secondary direction with a component perpendicular to the primary direction such that the internal pressure is increased in a region of the body part, and the compression unit at least partially encloses the body part, a perforation device, in particular a lancet or cannula, to produce a body opening in the area of the increased internal pressure.

Use of the compression unit according to the invention replaces the above-mentioned milking movement for squeezing out blood from the incision site in a simple and comfortable manner for the user. The compression unit not only yields larger quantities of body fluid than is the case with the compression devices of the prior art but the compression and withdrawal process is also considerably more pleasant for the patient. This is due to the fact that the compression unit fits snugly around the body part, in particular a finger. A further contributing factor is that the compression unit enables adequate quantities of body fluid to be obtained even with very small puncture depths.

The system according to the invention can be used particularly advantageously to obtain capillary blood from the finger pad. In addition it is also possible to withdraw blood or interstitial fluid from other body parts.

An essential element of the system is the compression unit which results in the body part being squeezed together not only in the direction of the primary applied pressure but also results in the applied pressure being at least partially diverted such that a squeezing occurs with components of force transverse to the primary direction and the compression unit (at least) partially encloses the body part. The mode of action of this advantageous compression is elucidated later on the basis of the embodiments. The compression unit produces an increase of the internal pressure in a first region 51 of the body part. This first region 51 of increased internal pressure adjoins the second region 53 on which the applied pressure acts. In the usual application case in which blood is removed from the finger, the finger is placed in the compression unit in such a manner that the finger tip from which the withdrawal is to take place juts out from the compression unit. The perforation can now take pace in the first region 51 of increased internal pressure (the finger tip) and body fluid can be removed. The perforation can be carried out by inserting a lancet or cannula in the case of a lancet it is preferably completely removed from the tissue after the incision to access the incision site from which the body fluid emerges. In the case of a cannula this can remain at the maximum puncture depth in order to convey body fluid from this depth or it can be withdrawn onto the skin surface in order to take up fluid from this position.

An increased internal pressure is generated using the compression unit according to the invention as is for example the case in the documents JP 9313465 and JP 9266889. However, a significant difference is that enclosure of a body part by the compression unit is achieved by converting a movement carried out by the user in a primary direction into a secondary movement. As a result it is not only possible to avoid motors and pumps and such like but the user also controls the procedure to a considerable extent which is found to be much more agreeable. In addition the action of the compression units according to the invention is also reversible in such a way that compression and enclosure of the body part stops immediately when the user removes the body part from the compression unit. Thus the user has full control of the procedure which in turn is found to be comfortable.

In preferred embodiments the compression unit has a so-called collapsing effect. This means that the user firstly perceives an increasing counter-pressure when he presses a body part (usually a finger) onto the compression unit which decreases again when a maximum counter-pressure is passed. The counter-pressure firstly increases when the body part is removed from the compression unit and then decreases again. This force time-course results in a relative minimum force when pressure is applied which enables the user to feel the prescribed pressing position. Furthermore due to the initially increasing pressure on removing the finger, the user is prompted to leave the body part in this position for the piercing; however, if he wishes he can also remove the body part without being significantly hindered in doing so.

In advantageous embodiments of the invention an analytical system is integrated into the system for withdrawing body fluid. Such analytical systems are well-known in the prior art. For example analytical systems named ACCUCHECK PLUS® and ACCUCHECK ADVANTAGE® are commercially available. As a rule analytical systems which are designed for consumers use disposable test elements which, after contact with a sample liquid, yield a signal which depends on the analyte concentration. In the field of blood sugar measurement optical test elements are used in which the reaction of glucose with a test chemistry leads to a change in colour as well as electrochemical test elements in which an enzymatic conversion of glucose enables an amperometric or potentiometric analysis. Test elements having a capillary gap can be advantageously used, the capillary gap of which can be contacted with the puncture site and take up body fluid there.

The system according to the invention simplifies the integration of a perforation device with an analytical system or for the first time makes an integration possible. As already stated it is customary in the prior art to manually press out the body fluid after producing a skin opening which means that the patient has to remove the body part from the perforation device. In contrast a system according to the present invention enables the patient to press the body part against the deformable compression unit and to leave it there in this compressed state to produce a skin opening as well as for the withdrawal. Hence a stronger degree of automation is possible in which the patient only has to press against the compression unit and all subsequent steps up to the read-out of the analytical result can proceed automatically.

A system according to the invention is preferably provided with a perforation device which is positioned close to the region of the body with increased internal pressure or can approach this region. Such perforation devices usually have a pressure-application region which allows the perforation device to be positioned and thus also a control of puncture depth. This pressure-application region is preferably pressed against the region of the body part having increased internal pressure using a weak spring. In this process a pressure of more than 5 N is to be avoided since body fluid, dammed up in the body part would be pressed out again. Suitable application pressures are in the range of circa 2 N.

Hence an integration of the perforation device and analytical system not only advantageously relates to a spatial integration but also a process integration which avoids operating steps by the user. Correspondingly such a system also advantageously has a control unit which coodinatively controls activation of the perforation device, withdrawal of body fluid and transport of body fluid to the analytical system and the analysis.

BRIEF DESCRIPTION OF THE DRAWINGS

FIGS. 1a and 1b show a compression unit into which a finger can be inserted, the compression unit having a bed of a substantially flexible material.

FIGS. 2a and 2b show a compression unit having a finger bed constructed of essentially inflexible half shells.

FIGS. 3a and 3b show a compression unit having a deformable material that has an essentially constant volume during deformation and is located in a frame.

DETAILED DESCRIPTION OF THE INVENTION

Figure 4:
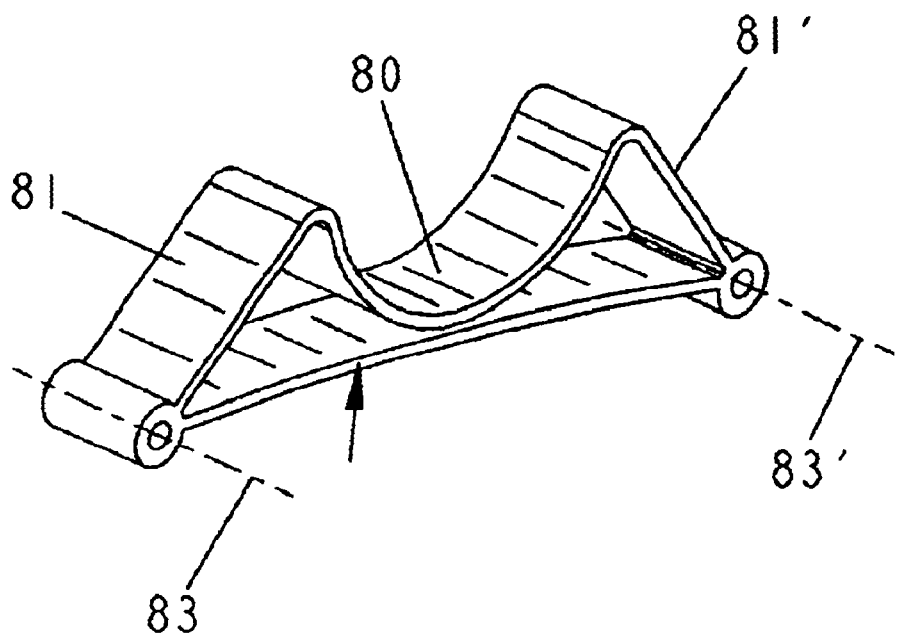
FIG. 4 is a perspective view of a compression unit manufactured from a plastic material.

FIG. 1 shows a compression unit into which a finger can be inserted such that the finger tip protrudes from the compression unit and the internal pressure is increased in the finger tip. The compression unit has a bed (80) made of a substantially flexible material and joints (81) made of a substantially rigid material between which joints the bed (80) is attached. The ends of the bed (80) are attached to the joints (81) in such a manner that it is arranged in a U-shape in the resting position. The ends of the joints which face away are pivoted on axes (83) that are fixed in space. When the finger is pressed against the compression unit in the primary movement direction (82), the bed (80) is pressed down and the joints (81) follow the downward movement of their ends that are linked to the bed which leads to a rotation around the axes (83). Rotation around these axes and the essentially constant length of the levers (81) results in a partial conversion of the primary movement (82) into a transverse secondary movement (84, 84') such that the finger is enclosed by the arms of the U-shaped region and is squeezed together.

FIG. 2 shows a similar embodiment to that of FIG. 1 in which, however, the finger bed (80) is constructed of essentially inflexible half shells (80a, 80b) which are connected together via a flexible region (85). When the finger is pressed into the bed (80a, 80b) there is again a rotation around the axes (83) such that the half shells move towards one another and the finger is pressed in between them. Also in this embodiment the movement of the half shells towards one another is achieved by a rotation of levers around an axis which is fixed in space.

An embodiment with a different construction is shown in FIG. 3. In this embodiment the compression unit comprises a deformable material (90) which however, has an essentially constant volume during deformation and is located in a frame (91) with an essentially constant structure. When the finger is pressed into the deformable material (90), the material moves away from it but, as a result of its constant volume, partially converts the primary movement into a secondary movement which results in the finger being at least partially surrounded and squeezed by the material.

FIG. 4 shows an embodiment which can be advantageously manufactured from a plastic for example in an injection moulding process. This arrangement like that of FIG. 1 has a bed (80) into which the finger is placed. The one piece injection moulded side pieces (81, 81') adopt the function of the levers. When a finger is pressed into the bed (80), the levers (81, 81') rotate around axes (83, 83') that are fixed in space and as a result of their constant length the upper region of the bed (80) is pressed together to enclose and squeeze the finger.

Figure 5:
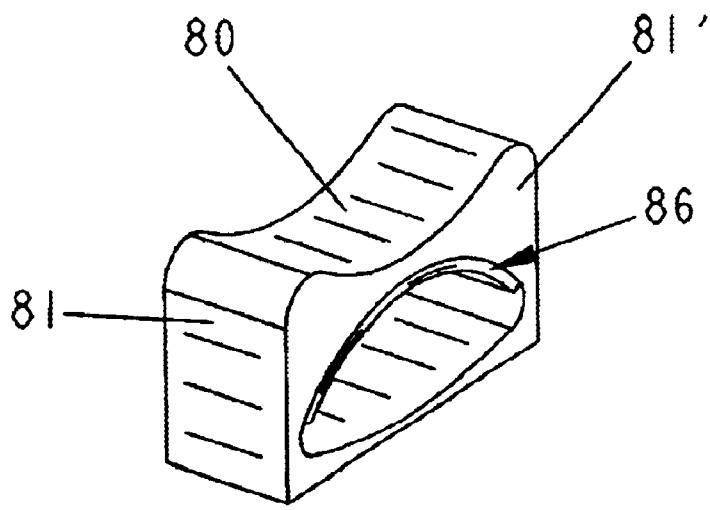
FIG. 5 is a perspective view of a compression unit manufactured from a flexible plastic.

FIG. 5 also shows an arrangement which can be manufactured in a simple manner from a flexible plastic such as a relatively solid rubber foam. When a finger is inserted into the bed (80) the bed is pressed down and the two side parts (81, 81') move towards one another such that the finger is enclosed. A leaf spring (86) can be advantageously integrated in such an embodiment which causes the above-mentioned collapsing effect. The leaf spring is tensioned by pressure being applied in the primary direction since counter-pressure is applied to its ends by the surrounding plastic. After passing through a planar shape the leaf spring folds into a tub shape in which the finger lies and is pressed together by the side parts (81, 81').

Figure 6A:
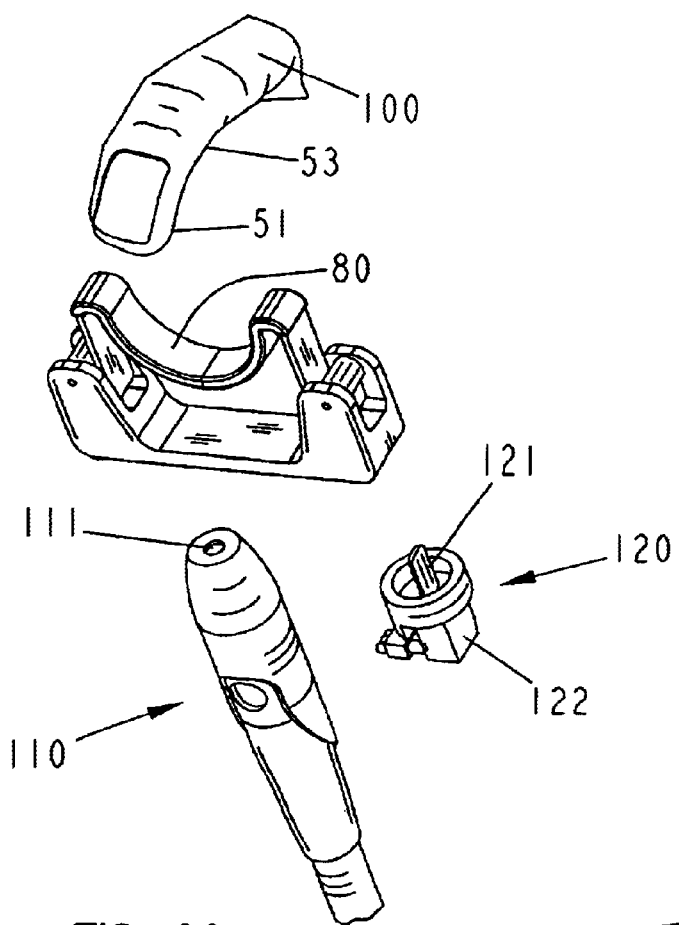
FIGS. 6a and 6b are perspective representations of the use of a compression unit of FIG. 1.
Figure 6B:
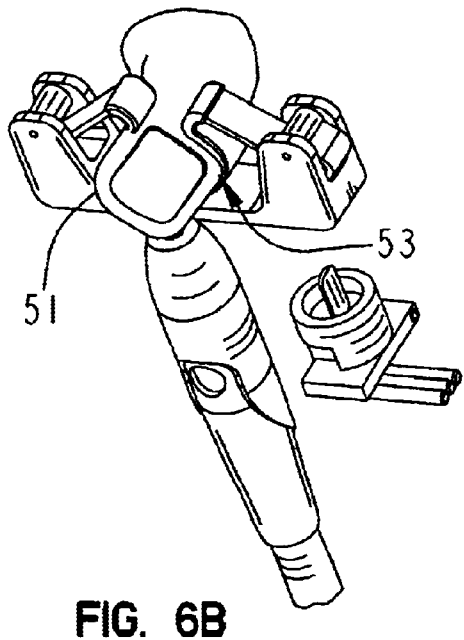

FIG. 6 shows the use of a compression unit of FIG. 1 in perspective representations A and B. The finger (100) is inserted into the bed (80) of the compression unit in such a manner that the compression unit closes by the applied pressure and results in blood congestion in the finger tip. As shown by the figures the user can determine to a large extent which part of the finger tip he presses against the perforation device (110). Even after the finger has been pressed i.e. in the position shown in FIG. 6B, the user can still vary the incision site to a large degree. The user receives a positive feedback on the incision site before carrying out the incision by the contact the finger feels with the pressure-application plate (111) of the perforation device. The blood withdrawal device SOFTCLIX® from the Roche Diagnostics Company can be used as the perforation device. It is of advantage when the perforation device used for this invention has an adjustable puncture depth. FIG. 6 additionally shows an analytical system (120) in which a test element (121) containing a capillary gap is located in the holder (122). After a perforation has been carried out in the position shown in FIG. 6B, the perforation device is moved away and the test element with the holder is moved to the perforation site such that it can take up body fluid. In the present case an electrochemical test element for glucose was used, the analysis of which by electrical measurements is well known and therefore does not have to be described in more detail here.

What is claimed is:

1. System for withdrawing body fluid from a first region of a part of the body, the system comprising:

a compression unit being formed to squeeze and at least partially enclose a second region of the body part when the body part is pressed against the unit in a primary direction, the second region adjoining the first region, and to partially convert applied pressure from the body part in the primary direction into a movement of the unit in a secondary direction with a component perpendicular to the primary direction such that an internal pressure is increased in the first region of the body part, a perforation device being formed to produce a body opening in the area of the increased internal pressure of the first region which juts out from the unit, wherein the puncture depth of the perforation device is adjustable, and a control unit is integrated which coordinatively controls the activation of the perforation device and analytical system.

2. System for stimulating the outflow of a body fluid from a first region of a body part comprising a compression unit which partially converts a pressure applied by a second region of the body part, which adjoins the first region, in a primary direction into a movement of the unit in a secondary direction with a component at right angles to the primary direction and thus increases the internal pressure in the first region of the body part, which juts out from the unit, wherein the compression unit squeezes and at least partially encloses the second region of the body part when the body part is pressed against the compression unit.

3. System as claimed in claim 2, in which the compression unit has a U-shaped region with side parts that are formed to move towards one another when the body part is pressed against the U-shaped region.

4. System for withdrawing body fluid from a first region of a part of the body, the system comprising:

a compression unit being formed to squeeze and at least partially enclose a second region of the body part when the body part is pressed against the unit in a primary direction, the second region adjoining the first region, and to partially convert applied pressure from the body part in the primary direction into a movement of the unit in a secondary direction with a component perpendicular to the primary direction such that an internal pressure is increased in the first region of the body part, and a perforation device being formed to produce a body opening in the area of the increased internal pressure of the first region, which juts out from the unit.

5. System as claimed in claim 4, in which the perforation device is displaceably disposed relative the compression unit.

6. System as claimed in claim 5, in which the perforation device is spring loaded.

7. System as claimed in claim 6, in which the puncture depth of the perforation device is adjustable.

8. System as claimed in claim 5, in which the puncture depth of the perforation device is adjustable.

9. System as claimed in claim 4, in which the puncture depth of the perforation device is adjustable.

10. System as claimed in claim 9, in which the analytical system contains at least one test element.

11. System as claimed in claim 4, in which an analytical system for the determination of the concentration of glucose is integrated.

12. System as claimed in claims 4, wherein the perforation device is a lancet or cannula.

13. System as claimed in claim 4, in which the compression unit has a U-shaped region with side parts that are formed to move towards one another when the body part is pressed against the U-shaped region.

14. System as claimed in claim 13, in which the compression unit is manufactured from a plastic or a rubber foam.

15. System as claimed in claim 4, in which the compression unit has a material that is deformable and has an essentially constant volume.

16. System as claimed in claim 15, further comprising a frame and the compression unit is arranged in the frame.

17. System for withdrawing body fluid from a region of a part of the body, the system comprising:

a compression unit being formed to at least partially enclose the body part when the body part is pressed against it in a primary direction and to partially convert applied pressure from the body part in the primary direction into a movement of the unit in a secondary direction with a component perpendicular to the primary direction such that an internal pressure is increased in the region of the body part, and a perforation device being formed to produce a body opening in the area of the increased internal pressure, in which the compression unit has a U-shaped region with side parts that are formed to move towards one another when the body part is pressed against the U-shaped region and the U-shaped region is flexible and includes ends that are connected to levers of essentially constant length.

18. System for withdrawing body fluid from a region of a part of the body, the system comprising:

a compression unit being formed to at least partially enclose the body part when the body part is pressed against it in a primary direction and to partially convert applied pressure from the body part in the primary direction into a movement of the unit in a secondary direction with a component perpendicular to the primary direction such that an internal pressure is increased in the region of the body part, and a perforation device being formed to produce a body opening in the area of the increased internal pressure, in which the compression unit has a U-shaped region with side parts that are formed to move towards one another when the body part is pressed against the U-shaped region and the U-shaped region is formed by two essentially inflexible half shells that are connected together via a flexible region.

19. Method for stimulating outflow of body fluid from a first region of a body part, the method comprising the steps of:

providing a compression unit, placing the body part in the unit so that the first region juts out from the unit, and pressing the body part against the compression unit in a primary direction, the compression unit squeezing and at least partially enclosing a second region of the body part and partially converting the primary pressing movement into a movement of the unit in a secondary direction transverse to the primary direction such that the internal pressure is increased in the first region of the body part.

20. Method of claim 19, wherein the body part is a finger pad.

21. Method as claimed in claim 19, in which the compression unit has a U-shaped region with side parts and the pressing step including pressing the body part against the U-shaped region to partially convert the primary pressing movement into movement of the side walls towards one another.

* * * * *